United States Patent [19]

Egusa et al.

[11] Patent Number: 5,256,423
[45] Date of Patent: Oct. 26, 1993

[54] METHOD FOR DESTROYING CYST OF NOXIOUS PLANKTON

[75] Inventors: Syuzo Egusa, Ichikawa; Yasuo Fukuyo, Matsudo, both of Japan

[73] Assignee: Katayama Chemical, Inc., Osaka, Japan

[21] Appl. No.: 771,441

[22] Filed: Oct. 4, 1991

[30] Foreign Application Priority Data

Oct. 12, 1990 [JP] Japan .................. 2-274651

[51] Int. Cl.$^5$ ............... A61K 33/40; A01N 39/00
[52] U.S. Cl. ................... 424/616; 424/613; 424/614; 424/615
[58] Field of Search ............... 424/616, 613, 614, 615

[56] References Cited

FOREIGN PATENT DOCUMENTS 55-141142 12/1980 Japan .

OTHER PUBLICATIONS

Murata, et al., "Screening of Removal Agents of a Red Tide Plankton *chattonella marina*-with Special Reference to the Ability of the Free Radicals Derived from the Hydrogen Peroxide and Polyunsaturated Fatty Acids", *Nippon Suisan Gakkaishi*, 1989, 55 (6) pp. 1075-1082.

*Primary Examiner*—Frederick E. Waddell
*Assistant Examiner*—F. Tsung
*Attorney, Agent, or Firm*—Bryan Cave

[57] ABSTRACT

A method for destroying cyst of noxious plankton, which comprises mixing in ballast water hydrogen peroxide or a compound producing the same and maintaining an effective concentration thereof for destroying cyst of noxious plankton.

9 Claims, No Drawings

METHOD FOR DESTROYING CYST OF NOXIOUS PLANKTON

BACKGROUND OF THE INVENTION

1. Field of the Invention

This invention relates to a method for destroying cyst of noxious plankton.

2. Prior Art

A ship having no or little load is difficult to maintain its equilibrium because of its lowered waterline. Therefore, such a ship is usually loaded with ballast water to maintain its equilibrium thereby assuring safe navigation thereof in the ocean. The ballast water is unloaded before the ship is loaded with cargo in a port of destination or before it arrives therein.

The ballast water is seawater pumped up and accommodated within a watertight compartment defined inside the ship for the above reason. The ballast water may include noxious plankton depending on the sea area from which it is pumped up, and may cause shellfish poison or red tide when discharged from the ship in the offing or harbor.

It is well known that a red tide due to an explosive multiplication of such noxious plankton pollutes the sea, causing fish and shellfish to die. This seriously damages the cultured fishery in particular. It is to use hydrogen peroxide, calcium peroxide or a peroxyhydrate as a controlling agent for red-tide plankton such as *Chattonella marina*, *Gymnodinium nagasakiense*, and the like [refer to Japanese Unexamined Patent Publication No. 141142/1980; "Screening of removal agents of a red tide plankton *Chattonella marina*—with special reference to the ability of free radicals derived from the hydrogen peroxide and polyunsaturated fatty acid", Nippon Suisan Gakkaishi 55 (6) 1075–1082 (1989); "Toxic effects of hydrogen peroxide on *Gymnodinium nagasakiense* and fishes", Bull, Fac. Bioreso, Mic Univ. No. 4 165–173 (1990)].

Various kinds of noxious plankton belonging to the following orders of classes are known.

1. Cyanophyceae
   (i) Chroococcales
   (ii) Nostocales
2. Cryptophyceae
   (i) Cryptomonadales
3. Dinophyceae
   (i) Prorocentrales
   (ii) Dinophysiales
   (iii) Gymnodiniales
   (iv) Noctilucales
   (v) Peridiniales
4. Bacillariophyceae
   (i) Centrales
      (i-i) Coscinodiscineae
      (i-ii) Rhizosoleniineae
      (i-iii) Biddulphiineae
   (ii) Pennales
      (ii-i) Araphidineae
      (ii-ii) Rhaphidineae
5. Raphidophyceae
   (i) Raphidomonadales
6. Chrysophyceae
   (i) Ochromonodales
   (ii) Pedinellales
   (iii) Dictyochales
7. Haptophyceae
   (i) Isochrysidales
   (ii) Prymnesiales
8. Euglenophyceae
   (i) Eutreptiales
   (ii) Euglenales
9. Prasinophyceae
   (i) Nephroselmidales
   (ii) Pterospermatales
   (iii) Pyramimonadales
10. Chlorophyceae
    (i) Volvocales The noxious plankton belonging to the above orders is classified into two types depending on its reproduction manner: asexual reproduction by binary fission, or sexual reproduction only between different mating types (+,−) to form cyst. The cyst in the latter corresponds to a seed of plant and germinates under certain conditions to become plankton. The exine of cyst is completely different from a cell wall of plankton in that it is extremely solid. Accordingly cyst can be in a dormancy for several years or more without dying even under severe conditions such as dark environment, oxygen-free environment and the like, under which plankton cannot be alive. Thus, the cyst is completely different from plankton in physiology, ecology and even morphology.

The phenomenon such that shellfish becomes poisonous due to shellfish-poisoning plankton has become tangible since 1987 or so in the sea off Japan. Recently, it was confirmed that cyst of shellfish-poisoning plankton was inhabiting the ballast water discharged from a Japanese oceangoing ship. Such cyst is presumed to be a cause of the occurrence of poisonous shellfish, and this problem is given consideration by other countries. Such a phenomenon has a tendency to be extended and prolonged, and hence it is desired to promptly take measures therefor and especially to develop an effective technical means.

The present inventors have investigated the facts so far known concerning the substance of the problem caused by the cyst of shellfish-poisoning plankton present in the ballast water. Although it is proved that shellfish is poisoned by the above-noted shellfish-poisoning plankton, there are things left unknown in the correlation between cyst and plankton. For example, the conditions, rate and time of germination of cyst are inconstant depending on the kind of cyst, and the dormancy period thereof is not precisely known yet. Further, tests revealed that cyst could not be destroyed by a plankton-destroying agent such as copper sulfate, montmorillonite or the like at a concentration for destroying plankton, by a ultrasonic treatment for a predetermined period of time for destroying the same, or by hydrogen peroxide under the conditions therefor.

SUMMARY OF THE INVENTION

Based on the foregoing investigation, the present inventors judged that for preventing a seawater pollution due to a red tide or shellfish poison caused by ballast water discharged from ships, destroying only noxious plankton present therein was insufficient and it was rather important to destroy the cyst of such plankton. This is because the cyst is considered to be an etiologic organism for such pollution.

The present inventors have made a wholehearted study on a method for directly and intensively destroying cyst of noxious plankton and reached the present invention.

Thus, the present invention provide a method for destroying cyst of noxious plankton, which comprises mixing in ballast water hydrogen peroxide or a compound producing the same and maintaining an effective concentration thereof for destroying cyst of noxious plankton.

DETAILED DESCRIPTION OF THE PREFERRED EMBODIMENTS

Hydrogen peroxide as used in the present invention is a safe agent free from a problem of residual toxicity or cumulative toxicity because of its high decomposability. Accordingly it causes no pollution if discharged in seawater upon or after the use thereof.

The compound producing hydrogen peroxide as used here is meant by a compound capable of producing hydrogen peroxide in water. Specifically, calcium peroxide, sodium percarbonate and the like can be mentioned.

It is preferred to sample pumped-up seawater or seawater present near the seabed in a sea area of which seawater is to be used as the ballast water to confirm the presence of cyst of noxious plankton before effecting the method of the invention.

The effective concentration for destroying cyst of noxious plankton as described above is generally about 10-1,000 ppm, preferably about 10-500 ppm in $H_2O_2$ equivalent concentration.

The period of time for maintaining the effective concentration of hydrogen peroxide (or a compound producing the same) depends on an initial concentration of hydrogen peroxide, temperature, amount of cyst, and the like. Generally speaking, the maintaining time is long when the concentration is relatively low while it is short when the concentration is relatively high. However, the maintenance of the effective concentration is needed for at least 3 hours, preferably for at least several hours. For example, the concentration of hydrogen peroxide should be maintained at about 10 ppm for at least 40 hours while at about 500 ppm for at least about 3 hours. In the case where the temperature of the ballast water is relatively low (for example, 15° C. or below), a longer maintenance at higher concentration is desired.

In general an ocean navigation takes a few weeks or more, and a coastal navigation takes several hours to several ten hours. Hence, a sufficient cyst-destroying treatment can be conducted during the navigation by adjusting the concentration of hydrogen peroxide and the time for maintaining the same.

The ballast water may includes cyst of shellfish-poisoning plankton together with the plankton of the same species. It was confirmed that effecting the method of the present invention to such ballast water completely destroyed the plankton before destroying cyst cell.

The method of the invention works well for destroying cyst of red-tide plankton as well. Accordingly it is possible to conduct desired destruction thereof by directly introducing hydrogen peroxide (or a compound producing the same).into the sea near the seabed around which cyst of red-tide plankton is present, or mixing the same in seawater pumped up therefrom.

EXAMPLE

Hereinafter, the present invention will be more fully described with reference to Examples which are merely examples and not limitative of the invention.

EXAMPLE 1

A muddy deposit accumulated on the surface of seabed was sampled with a bottom sampler, sieved with 125 micron mesh to remove impurities, and further sieved with 37 micron mesh and washed with filtered seawater to collect cysts of plankton. From the collected those of noxious plankton of a desired kind were selected using a microscope.

For examining the relationship between the concentration of hydrogen peroxide and the time period for contacting hydrogen peroxide with cyst, cysts of *Polykrikos schwatzii* belonging to Dinophyceae Gymnodiniales were selected and groups of ten individuals thereof were placed respectively in solutions of hydrogen peroxide diluted with filtered seawater at predetermined concentrations, each of the solutions being in a watch glass of 7 cm diameter in an amount of 3 ml. The cysts were contacted with hydrogen peroxide for 3, 24 and 48 hours, then washed three times with filtered seawater. Each of the cysts was placed in 1 ml of newly filtered seawater in a multiwellplate and cultured in a thermostat at 22°-25 ° C. At every elapse of predetermined time the cysts were observed under microscope with respect to their state and germination rate. The result of the observation is shown in Table 1.

TABLE 1

| $H_2O_2$ concentration (ppm) | Time for contacting an agent with cyst (hr) | Number of germinated cysts with elapse of time | | | |
|---|---|---|---|---|---|
| | | 24 hr | 48 hr | 72 hr | 96 hr |
| 0 | — | 2 | 3 | 4 | 4 |
| 10 | 3 | 1 | 1 | 2 | 2 |
|  | 24 | 1 | 1 | 1 | 1 |
|  | 48 | 0 | 0 | 0 | 0 |
| 20 | 3 | 0 | 1 | 1 | 1 |
|  | 24 | 0 | 0 | 0 | 0 |
|  | 48 | 0 | 0 | 0 | 0 |
| 50 | 3 | 0 | 0 | 1 | 1 |
|  | 24 | 0 | 0 | 0 | 0 |
|  | 48 | 0 | 0 | 0 | 0 |
| 100 | 3 | 0 | 0 | 0 | 0 |
|  | 24 | 0 | 0 | 0 | 0 |
|  | 48 | 0 | 0 | 0 | 0 |
| 500 | 3 | 0 | 0 | 0 | 0 |
|  | 24 | 0 | 0 | 0 | 0 |
|  | 48 | 0 | 0 | 0 | 0 |

Note:
It is judged that the case where 4 or more cysts are germinated among 10 cysts is normal.
Remark:
In accordance with the method of the invention, no germination was observed after 96 hr.

EXAMPLE 2

Cysts of *Alexandriumu catenella* belonging to Dinophyceae Peridiniales were selected in the same manner as in Example 1. The cysts were cultured, then observed also in the same manner as in Example 1. The result of the observation is shown in Table 2.

TABLE 2

| $H_2O_2$ concentration (ppm) | Time for contacting an agent with cyst (hr) | Number of germinated cysts with elapse of time | | | |
|---|---|---|---|---|---|
| | | 24 hr | 48 hr | 72 hr | 96 hr |
| 0 | — | 2 | 4 | 5 | 5 |
| 10 | 3 | 2 | 2 | 2 | 2 |
|  | 24 | 1 | 1 | 2 | 2 |
|  | 48 | 0 | 0 | 0 | 0 |
| 20 | 3 | 0 | 1 | 1 | 2 |
|  | 24 | 0 | 0 | 0 | 0 |

TABLE 2-continued

| $H_2O_2$ concentration (ppm) | Time for contacting an agent with cyst (hr) | Number of germinated cysts with elapse of time | | | |
|---|---|---|---|---|---|
| | | 24 hr | 48 hr | 72 hr | 96 hr |
| | 48 | 0 | 0 | 0 | 0 |
| 50 | 3 | 0 | 1 | 1 | 1 |
| | 24 | 0 | 0 | 0 | 0 |
| | 48 | 0 | 0 | 0 | 0 |
| 100 | 3 | 0 | 0 | 0 | 0 |
| | 24 | 0 | 0 | 0 | 0 |
| | 48 | 0 | 0 | 0 | 0 |
| 500 | 3 | 0 | 0 | 0 | 0 |
| | 24 | 0 | 0 | 0 | 0 |
| | 48 | 0 | 0 | 0 | 0 |

Note:
It is judged that the case where 4 or more cysts are germinated among 10 cysts is normal.
Remark:
In accordance with the method of the invention, no germination was observed after 96 hr.

EXAMPLE 3

Cysts of *Alexandriumu tamarense* belonging to Dinophyceae Peridiniales were selected in the same manner as in Example 1. The cysts were cultured, then observed also in the same manner as in Example 1. The result of the observation is shown in Table 3.

TABLE 3

| $H_2O_2$ concentration (ppm) | Time for contacting an agent with cyst (hr) | Number of germinated cysts with elapse of time | | | |
|---|---|---|---|---|---|
| | | 24 hr | 48 hr | 72 hr | 96 hr |
| 0 | — | 2 | 3 | 4 | 4 |
| 10 | 3 | 1 | 2 | 2 | 2 |
| | 24 | 1 | 1 | 2 | 2 |
| | 48 | 0 | 0 | 0 | 0 |
| 20 | 3 | 1 | 1 | 1 | 1 |
| | 24 | 0 | 0 | 0 | 0 |
| | 48 | 0 | 0 | 0 | 0 |
| 50 | 3 | 0 | 0 | 1 | 1 |
| | 24 | 0 | 0 | 0 | 0 |
| | 48 | 0 | 0 | 0 | 0 |
| 100 | 3 | 0 | 0 | 0 | 0 |
| | 24 | 0 | 0 | 0 | 0 |
| | 48 | 0 | 0 | 0 | 0 |
| 500 | 3 | 0 | 0 | 0 | 0 |
| | 24 | 0 | 0 | 0 | 0 |
| | 48 | 0 | 0 | 0 | 0 |

Note:
It is judged that the case where 4 or more cysts are germinated among 10 cysts is normal.
Remark:
In accordance with the method of the invention, no germination was observed after 96 hr.

EXAMPLE 4

Using a setup assuming an actual ballast tank, the relation between the concentration of hydrogen peroxide and cyst-destroying effect was tested according to the following test method.

Test Method

A muddy sea deposit (10 g) including cysts of *Alexandriumu catenella* was placed in a watertight iron tank (1×1×1 m) of which inner surface was coated with epoxy resin. Then, 1 m³ of unfiltered seawater containing 17.5 mg/l of hydrogen peroxide was poured into the tank so that the deposit may be mixed well therein. Thereafter, the tank was sealed and moored in the sea with a portion kept emerging from the sea surface by ⅓. Every elapse of a predetermined time a deposit and seawater were sampled in a small amount and observed under microscope with respect to the concentration of hydrogen peroxide and germination rate of cysts. The result of the test is shown in Table 4.

TABLE 4

| | Elapse of time (hr) | | | | | | |
|---|---|---|---|---|---|---|---|
| | 0 | 10 | 20 | 30 | 40 | 50 | 240 |
| $H_2O_2$ concentration (ppm) | 17.50 | 15.75 | 13.65 | 12.00 | 10.00 | 9.50 | N. D |
| Germination rate (number of geminated cysts/number of sampled cysts) | 7/10 | 4/9 | 2/8 | 1/11 | 0/10 | 0/9 | 0/9 |
| Temperature of ballast water (°C.) | 23.5 | 25.4 | 25.0 | 24.7 | 25.8 | 25.3 | 25.9 |

Note:
N. D means "Not Detected".

As has been described, the method of the present invention in which the concentration of hydrogen peroxide is maintained at a predetermined value can effectively destroy cyst of noxious plankton. Hence, treating ballast water pumped up in a ship in accordance with the present method to destroy cyst of noxious plankton existing therein or to inhibit germination thereof enables to prevent problems such as shellfish poison and the like even if the ballast water is discharged at a port or offing.

Thus, the present invention is applicable to treatments of various seawater systems in which not only noxious plankton but also cyst thereof is present or only the cyst is present. Especially the present invention is highly useful in treating ballast water in which noxious plankton is difficult to grow due to lack of sunlight and cyst thereof alone is alive, since cyst of noxious plankton such as shellfish-poisoning plankton can be destroyed by the treatment before the ballast water is discharged.

What is claimed is:

1. A method of preventing contamination of navigable waters by cysts of noxious plankton contained in ballast water discharged from the ballast of a ship, said method comprising adding an amount of hydrogen peroxide, or a compound which produces hydrogen peroxide, to said ballast to create a concentration of hydrogen peroxide in the ballast water contained therein which is effective in destroying cysts, and holding said ballast water containing the hydrogen peroxide in the ballast for a period of time sufficient to destroy cysts of noxious plankton present in said ballast water prior to discharging said ballast water into navigable waters.

2. The method as set forth in claim 4, wherein said effective concentration ranges from about 10 ppm to about 500 ppm in $H_2O_2$ equivalent concentration.

3. The method of claim 2, wherein said effective concentration in the ballast water is held for at least 3 hours.

4. The method of claim 3, wherein said effective concentration in the ballast water is held for a period of time of from at least 3 to about 48 hours.

5. A method of preventing contamination of navigable waters by cysts of noxious plankton contained in ballast water discharged from the ballast of a ship, said method comprising adding an amount of hydrogen peroxide, or a compound which produces hydrogen peroxide, to said ballast to create a concentration of hydrogen peroxide in the ballast water contained therein of from about 100 to about 500 ppm of $H_2O_2$ and holding said ballast water containing the hydrogen peroxide in the ballast for a period of time sufficient to destroy cysts of noxious plankton present in said ballast water prior to discharging said ballast water into navigable waters.

6. The method of claim 5, wherein said effective concentration in the ballast water is held for at least 3 hours.

7. The method of claim 6, wherein said concentration in the ballast is held for at least 3 to about 48 hours.

8. The method of claim 7, wherein said concentration in the ballast water is held for at least 3 to about 24 hours.

9. The method as set forth in claim 1, wherein the $H_2O_2$ equivalent concentration is maintained at a value of from 10 to 500 ppm for a predetermined period of time ranging from 3 to 40 hours.

* * * * *